United States Patent [19]

Aoki et al.

[11] 4,279,990
[45] Jul. 21, 1981

[54] COLOR PHOTOGRAPHIC MATERIALS

[75] Inventors: Kozo Aoki; Nobuo Furutachi; Satoru Sawada, all of Minami-ashigara, Japan

[73] Assignee: Fuji Photo Film Co., Ltd., Minami-ashigara, Japan

[21] Appl. No.: 185,848

[22] Filed: Sep. 10, 1980

[30] Foreign Application Priority Data

Sep. 10, 1979 [JP] Japan .................................. 54-116283

[51] Int. Cl.³ .............................................. G03C 1/40
[52] U.S. Cl. ...................... 430/551; 430/372; 430/564
[58] Field of Search ...................... 430/372, 551, 564

[56] References Cited

U.S. PATENT DOCUMENTS

| | | | |
|---|---|---|---|
| 2,515,121 | 7/1950 | Harsh et al. | 430/372 |
| 2,647,057 | 7/1953 | Seary et al. | 430/372 |
| 2,726,955 | 12/1955 | Parnell | 430/564 |
| 3,930,866 | 1/1976 | Oishi et al. | 430/551 |
| 4,015,990 | 4/1977 | Ishida et al. | 430/551 |

Primary Examiner—J. Travis Brown
Attorney, Agent, or Firm—Sughrue, Rothwell, Mion, Zinn and Macpeak

[57] ABSTRACT

Discoloring and fading of silver halide color photographic materials are effectively prevented by incorporating a compound of the formula (I) or (II) in a silver halide photographic layer thereof

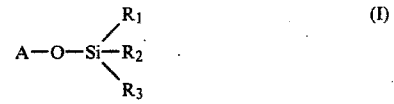

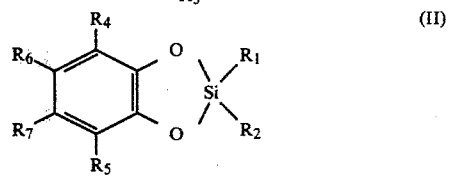

wherein A represents an aryl group; $R_1$, $R_2$ and $R_3$ each represents hydrogen, a halogen atom, an alkyl group, or an aryl group, except that $R_1$, $R_2$ and $R_3$ cannot all be hydrogen atoms; $R_4$ and $R_5$ each represents hydrogen, a halogen atom, an alkyl group, an aryl group, an alkoxy group, an alkylthio group, an acyl group, an aryloxy group, a carboxy group, a sulfo group or a hydroxy group; and $R_6$ and $R_7$ each represents hydrogen, a halogen atom, an alkyl group, an aryl group, an alkoxy group, an aryloxy group, an alkylthio group, an acyl group, or a hydroxy group; or $R_6$ and $R_7$ together form an

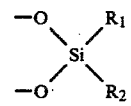

group or a 5-membered or 6-membered carbocyclic or heterocyclic ring.

11 Claims, No Drawings

COLOR PHOTOGRAPHIC MATERIALS

BACKGROUND OF THE INVENTION

1. Field of the Invention

This invention generally relates to color photographic materials, and more particularly, to color photographic materials wherein the fading of dye images obtained and discoloring of uncolored portions (i.e., unexposed portions, hereinafter referred to as white ground) are prevented.

2. Description of the Prior Art

Color images obtained by processing silver halide color photographic material are generally composed of azomethine dyes or indoaniline dyes formed by the reaction of the oxidation product of an aromatic primary amine developing agent and couplers.

It is generally desirable that the color photographic images thus-obtained be preserved for a long period of time as a record or for exhibition, but these photographic images are not always stable to light and humidity, and hence when the color images are exposed to light for a long period of time, or preserved under conditions of high temperature and high humidity for a long period of time, fading or discoloring of the color images and discoloring of the white ground usually occurs, causing deterioration of the image quality.

Such fading or discoloring of images can be fatal defects in image recording materials. Certain compounds tending to overcome these difficulties have higherto been used. Examples include hydroquinone derivatives such as 2,5-di-tert-butylhydroquinone, etc.; phenol compounds such as 2,6-di-tert-butyl-p-cresol, 4,4'-methylenebis(2,6-di-tert-butylphenyl), 2,2'-methylenebis(4-ethyl-6-tert-butylphenol), 4,4'-isopropylidenediphenol, etc.; and compounds such as tocopherol, etc. Also, compounds formed by acylating or alkylating the hydroxy groups of these phenolic compounds, tocopherol compounds, and hydroquinone derivatives have recently been prepared.

These compounds may exhibit some effect for preventing the occurrence of fading or the discoloring of dye images, but these compounds also have disadvantages, in that the effect is low, or, if they have a strong effect for the prevention of fading, they adversely affect color hue, form fog, cause poor dispersion, and/or form crystals. Thus, dye image stabilizers which exhibit excellent properties in all photographic aspects have not yet been found.

SUMMARY OF THE INVENTION

An object of this invention is to provide a color photographic material capable of providing stabilized color images by incorporating in photographic light-sensitive emulsion layers a dye image stabilizer which does not cause deterioration in color hue and formation of fog and which has a sufficient effect for preventing the occurrence of fading and discoloring of color images.

Other object of this invention is to provide a color photographic material that exhibits less yellow stain by incorporating in the photographic light-sensitive emulsion layers a compound having a sufficient effect of preventing the occurrence of yellow stain in both image and non-image portions caused by the exposure of the color image to light.

As a result of extensive investigations, it has now been found that the above-described objects of this invention can be attained by incorporating at least one of the compounds represented by the formula (I) or (II) in the photographic layers of a color photographic material

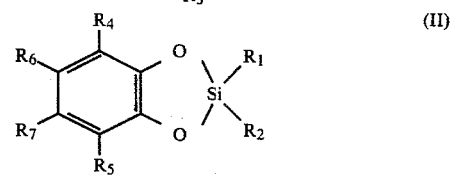

wherein A represents an aryl group; $R_1$, $R_2$ and $R_3$ each represents hydrogen, a halogen atom, an alkyl group, or an aryl group, except that $R_1$, $R_2$ and $R_3$ cannot all be hydrogen; $R_4$ and $R_5$ each represents hydrogen, a halogen atom, an alkyl group, an aryl group, an alkoxy group, an alkylthio group, an acyl group, an aryloxy group, a carboxy group, a sulfo group or a hydroxy group; and $R_6$ and $R_7$ each represents hydrogen, a halogen atom, an alkyl group, an aryl group, an alkoxy group, an aryloxy group, an alkylthio group, an acyl group, or a hydroxy group; or $R_6$ and $R_7$ together form an

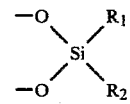

group or a 5-membered or 6-membered carbocyclic or heterocyclic ring.

DETAILED DESCRIPTION OF THE INVENTION

In the formula (I), A represents an aryl group, more specifically, a substituted or unsubstituted phenyl or naphthyl group or a chroman, spirochroman, indan or spiroindan ring having a substituent

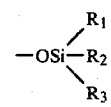

on the phenyl moiety thereof.

In the formula (I), A represents a substituted or unsubstituted phenyl or naphthyl group. Examples of the substituents that may be present on the above groups are: a halogen atom; a nitro group; a cyano group; a thiocyano group; a mercapto group; a hydroxy group; an

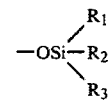

group; straight chain, branched chain, or cyclic alkyl group having from 1 to 32 carbon atoms (e.g., methyl, ethyl, isopropyl, t-butyl, n-octyl, t-octyl, dodecyl, t-amyl, 1,1-dimethylbutyl, cyclohexyl, hexadecyl, benzyl, etc.); an alkoxy group having from 1 to 32 carbon atoms (e.g., methoxy, ethoxy, n-octyloxy, t-octyloxy, 2-ethylhexyloxy, dodecyloxy, hexadecyloxy, octadeoxy, benzyloxy, etc.); an aryl group having from 6 to 32 carbon atoms (e.g., phenyl group, naphthyl group, etc.); an acyl group having from 1 to 32 carbon atoms (e.g., acetyl, octanoyl, tetradecanoyl, benzoyl, etc.); an acylamino group having from 1 to 32 carbon atoms (e.g., acetamido, tetradecanamido, benzamido, etc.); a sulfonamido group having from 1 to 32 carbon atoms (e.g., methanesulfonamido, ethanesulfonamido, benzenesulfonamido, etc.); an alkoxycarbonyl group having from 1 to 32 carbon atoms (e.g., a methoxycarbonyloxy, benzyloxycarbonyl, etc.); an aryloxycarbonyl group having from 7 to 32 carbon atoms (e.g., phenoxycarbonyl, α-naphthoxycarbonyl, etc.); an alkoxycarbonyloxy group having from 1 to 32 carbon atoms (e.g., methoxycarbonyloxy, ethoxycarbonyloxy, etc.); an aryloxycarbonyloxy group having from 7 to 32 carbon atoms (e.g., phenoxycarbonyloxy, etc.); an acyloxy group having from 1 to 32 carbon atoms (e.g., acetyloxy, butanoyloxy, benzyloxy, etc.); an alkoxycarbonylamino group having from 1 to 32 carbon atoms (e.g., methoxycarbonylamino, propoxycarbonylamino, etc.); an aryloxycarbonylamino group having from 7 to 32 carbon atoms (e.g., phenoxycarbonylamino, etc.); an alkylthio group having from 1 to 32 carbon atoms (e.g., methylthio, n-octylthio, n-dodecylthio, n-octadecylthio, etc.), an arylthio group having from 6 to 32 carbon atoms (e.g., phenylthio, naphthylthio, etc.); an alkylsulfonyl group having from 1 to 32 carbon atoms (e.g., ethylsulfonyl, n-dodecylsulfonyl, n-tetradecylsulfonyl, etc.); an arylsulfonyl group having from 6 to 32 carbon atoms (e.g., benzenesulfonyl, etc.); an alkylsulfonyloxy group having from 1 to 32 carbon atoms (e.g., methylsulfonyloxy, n-octylsulfonyloxy, n-tetradecylsulfonyloxy, etc.); an arylsulfonyloxy group having from 6 to 32 carbon atoms (e.g., phenylsulfonyloxy, etc.); and a heterocyclic group (e.g., triazinyl, 1-imidazolyl, etc.). These substituents may further be substituted by, for example, a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, and a mercapto group (these substituents are hereinafter referred to as "Substituents S").

A in the formula (I) may also represent a chroman, spirochroman, indan or spiroindan ring having the substituent

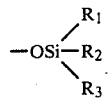

on the phenyl moiety thereof.

$R_1$, $R_2$ and $R_3$ in the formulae (I) and (II) each represents hydrogen; a halogen atom (e.g., chlorine atom, bromine atom, etc.); an alkyl group having from 1 to 32 carbon atoms (e.g., methyl, ethyl, i-propyl, t-butyl, etc.); or an aryl group having from 6 to 32 carbon atoms (e.g., phenyl, naphthyl, etc.) and the alkyl and aryl groups may have a further substituent, one or more substituents selected from those described above for A (i.e., Substituents S).

$R_4$ and $R_5$ in the formula (II) may each represent an alkyl group having from 1 to 32 carbon atoms (e.g., methyl, ethyl, i-propyl, t-butyl, t-octyl, n-octyl, n-dodecyl, etc.); an aryl group having from 6 to 32 carbon atoms (e.g., phenyl, naphthyl, etc.); an alkoxy group having from 1 to 32 carbon atoms (e.g., methoxy, ethoxy, n-butoxy, 2-ethylhexyloxy, n-octyl, n-tetradecyloxy, etc.); an alkylthio group having from 1 to 32 carbon atoms (e.g., methylthio, n-octylthio, n-dodecylthio, n-hexadecylthio, etc.); an acyl group having from 1 to 32 carbon atoms (e.g., acyl, benzoyl, n-octanoyl, tetradecanoyl, etc.); and an aryloxy group having from 6 to 32 carbon atoms (e.g., phenoxy, α-naphthoxy, etc.). These groups may be substituted by one or more substituents selected from those described above for A (i.e., Substituents S). $R_4$ and $R_5$ may each further represent hydrogen, a halogen atom (e.g., fluorine atom, chlorine atom, bromine atom, etc.), a carboxy group, a sulfo group, or a hydroxy group.

$R_6$ and $R_7$ in the formula (II) can represent an alkyl group having from 1 to 32 carbon atoms (e.g., methyl, ethyl, t-butyl, t-octyl, n-hexadecyl, benzyl, cyclohexyl, etc.); an aryl group having from 6 to 32 carbon atoms (e.g., phenyl, naphthyl, etc.); an alkoxy group having from 1 to 32 carbon atoms (e.g., methoxy, ethoxy, benzyloxy, n-hexyloxy, n-dodecyloxy, etc.); an aryloxy group having from 7 to 32 carbon atoms (e.g., phenoxy, α-naphthoxy, etc.); an alkylthio group having from 1 to 32 carbon atoms (e.g., methylthio, n-hexylthio, tetradecylthio, etc.); or an acyl group having from 1 to 32 carbon atoms (e.g., acetyl, benzoyl, butanoyl, octanoyl, etc.). These groups may be substituted by one or more of the substituents selected from those described above in regard to A (i.e., Substituents S). $R_6$ and $R_7$ may further represent hydrogen, a halogen atom (e.g., a fluorine atom, a chlorine atom, etc.), or a hydroxy group. Still further, $R_6$ and $R_7$ together may form an

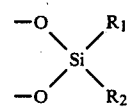

group (wherein $R_1$ and $R_2$ have the same meaning as described above in regard to A) or a 5-membered or 6-membered carbocyclic or heterocyclic ring. Examples of the carbocyclic rings condensed with the benzene ring of the formula (II) include an indian ring, a tetrahydronaphthalene ring, etc., and examples of heterocyclic rings condensed with the benzene ring of the formula (II) include a chroman ring, a coumaran ring, a spirochroman ring, and so forth.

In preferred compounds according to the formula (I), A is a substituted phenyl, and the substituent on the phenyl group is preferably a halogen atom, an alkyl group, an alkoxy group, an alkoxycarbonyl group, an acyloxy group, an alkoxycarbonyloxy group, an alkylthio group or a hydroxy group as stated above in regard to A, and $R_1$, $R_2$ and $R_3$ are unsubstituted alkyl groups or aryl groups as discussed above in regard to $R_1$, $R_2$ and R₃. Other preferred examples of A are a chroman, spirochroman, indan or spiroindan ring having an

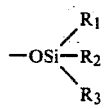

group substituted on the phenyl moiety.

In preferred compounds according to the formula (II), R₄ and R₅ are hydrogen, a halogen atom, an alkyl group, an alkoxy group, or an alkylthio group as described above in regard to R₄ and R₅, and R₆ and R₇ each can be hydrogen, a halogen atom, an alkyl group, an alkoxy group, an alkylthio group, or a hydroxy group; or R₆ and R₇ together form an

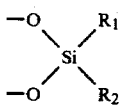

group (wherein R₁ and R₂ are preferably an unsubstituted alkyl or aryl groups). In compounds of the formula (II) wherein R₆ and R₇ form a ring, preferred examples of such rings condensed with the benzene ring of the formula (II) are a chroman ring and a spirochroman ring.

The compounds according to the formulae (I) and (II) are particularly effective when they are used together with a magenta coupler, and particularly a 5-pyrazolone series couplers, such as in a green-sensitive silver halide emulsion layer, or with a cyan coupler, particularly a phenol or naphthol derivatives, as in a red-sensitive silver halide emulsion layer.

Furthermore, the compounds according to the formulae (I) and (II) can be used together with the known fading prevention agents such as hydroquinone derivatives, hydroxychroman derivatives, hydroxyspirochroman derivatives, alkoxychroman derivatives, alkoxyspirochroman derivatives, and alkoxyphenol derivatives.

Typical examples of these compounds are illustrated below, but the compounds used in this invention are not limited to these compounds.

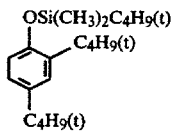

(1)

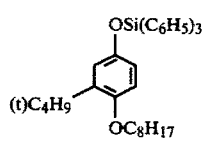

(2)

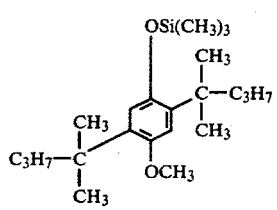

(3)

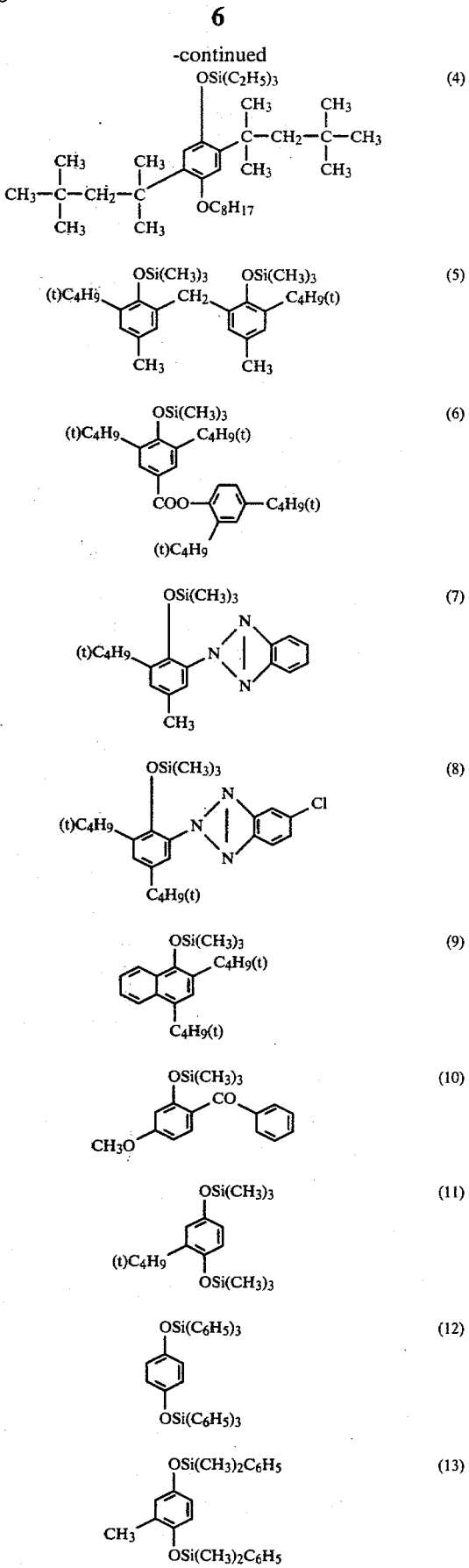

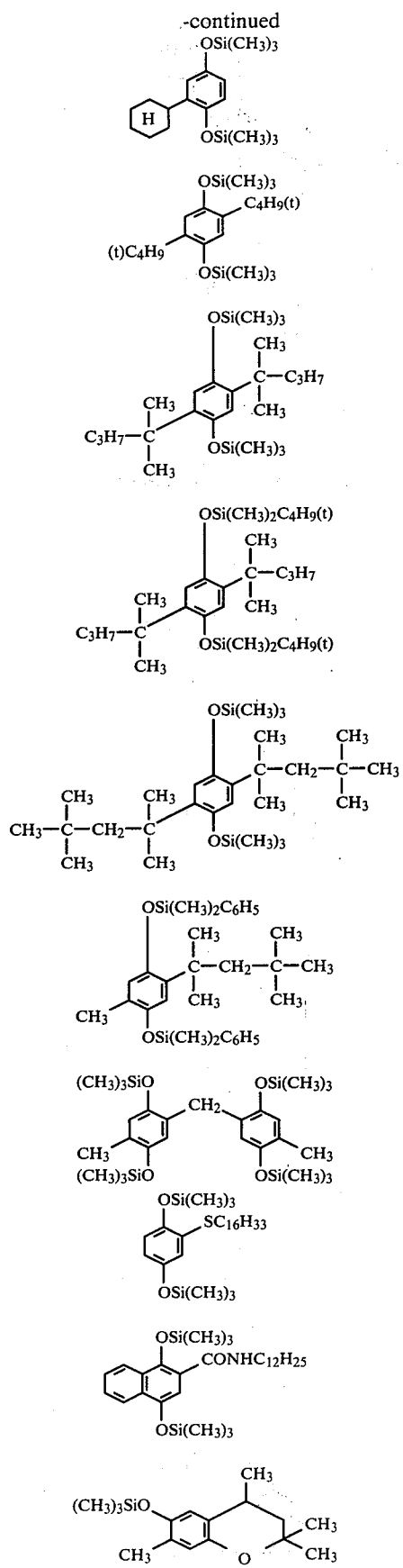
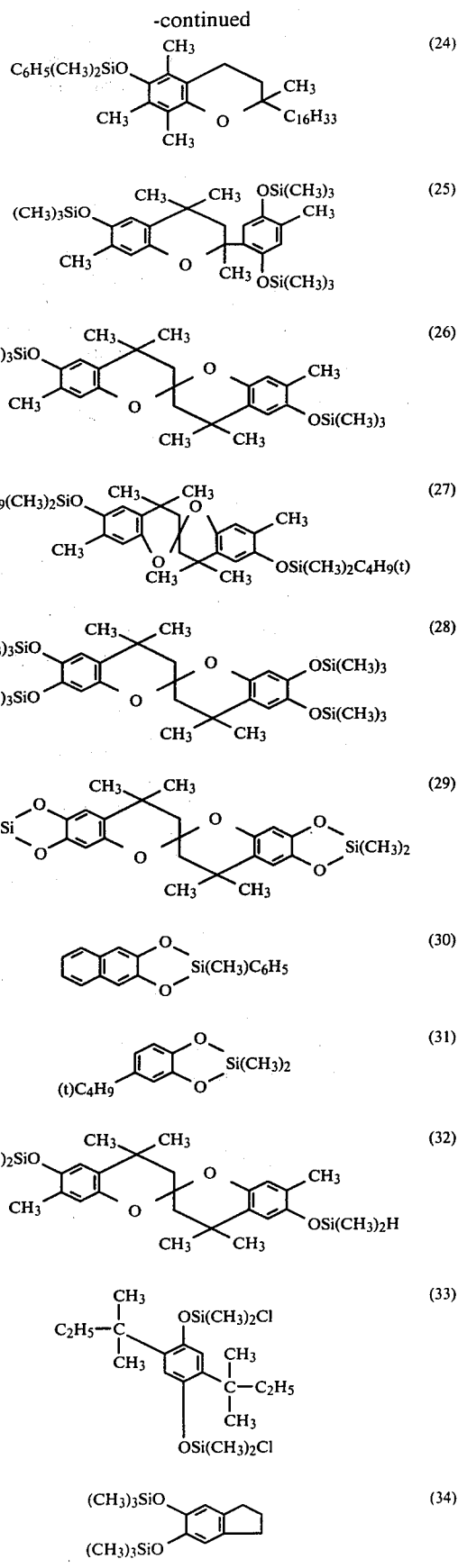

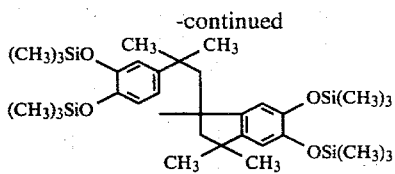

(35)

In general, various synthesis methods for silyl ether are known for providing a protective group for the hydroxy group. For example, there are a method using a chlorosilane and a deoxidizer such as pyridine, triethylamine, etc. (see, *J. Org. Chem.*, Vol. 22, p. 592 (1957), *J. Amer. Chem. Soc.*, Vol. 88, p. 3390 (1966), *Tetrahedron Lett.*, p. 317 (1973), *Synthetic Comm.*, Vol. 1, p. 81 (1971), and *J. Amer. Chem. Soc.*, Vol. 93, p. 7319 (1971)), and a method using silazanes such as hexamethyldisilazane or a dilylacetamide (see, e.g., *Chem. Comm.*, p. 466 (1968) and *J. Med. Chem.*, Vol. 16, p. 54 (1973)). Also, there is a method using a dichlorosilane and a deoxidizer such as pyridine (see, e.g., *Tetrahedron Lett.*, p. 967 (1969)).

The compounds of this invention can be produced by the methods as shown by the following general reactions (III) or (IV) according to the descriptions provided in the above-cited literature:

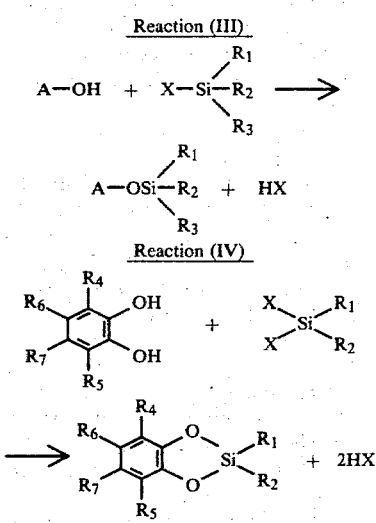

wherein A, $R_1$, $R_2$, $R_3$, $R_4$, $R_5$, $R_6$ and $R_7$ have the same meaning as described above and X represents a halogen atom.

For example, compounds according to this invention can be easily obtained by dissolving the compound of A-OH or

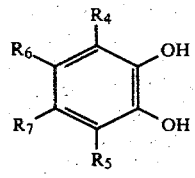

in a hydrocarbon solvent (e.g., n-hexane, benzene, etc.) or a nonprotonic polar solvent (e.g., dimethylformamide, etc.), adding thereto a compound of

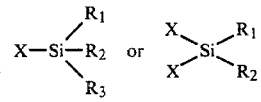

respectively, in an amount of from 1/1 to 10/1 (molar ratio of Si-compound to A-OH compound or catecholic compound), and a basic catalyst (e.g., pyridine, triethylamine, etc.) in an amount of from 1/1 to 20/1 (molar ratio of basic catalyst to A-OH compound or catecholic compound), and reacting them at a temperature range of −10° C. to 50° C. Practical examples will become apparent by the following synthesis examples. That is, practical synthesis examples of typical compounds of this invention are shown below, but it will be easily understood that other compounds of this invention can be also prepared in a similar manner.

SYNTHESIS EXAMPLE 1

Synthesis of Compound (3), 2,5-di-t-hexyl-4-methoxyphenyltrimethylsilyl ether 10.0 g (0.034 mol) of 2,5-di-t-hexyl-4-methoxyphenyl was dissolved in 70 ml of methylene chloride, and then 3.2 ml (0.041 mol) of pyridine was added to the solution. Thereafter, 4.1 g (0.037 mol) of chlorotrimethylsilane was added dropwise to the mixture while maintaining the mixture at from 10° to 20° C. Then, the mixture was stirred for one hour at 20° to 25° C. and the precipitates formed were separated by filtration. By distilling off the solvent under reduced pressure, a colorless oily product having a solidifying point of about 20° C. was obtained (yield: about 100%).

Elemental Analysis: Calcd.: C 72.48%; H 11.06%. Found: C 72.62%; H 11.04%.

SYNTHESIS EXAMPLE 2

Synthesis of Compound (16), 2,5-di-t-hexyl-1,4-phenylenebis(trimethylsilyl) ether 13.9 g (0.05 mol) of 2,5-di-t-hexylhydroquinone was dissolved in 100 ml of methylene chloride, and then 9.5 ml (0.06 mol) of pyridine was added to the solution. 12 g (0.055 mol) of chlorotrimethylsilane was added to the mixture and the resultnat mixture was treated in the same manner as Synthesis Example 1 above, and 21 g of crystals were thereby obtained. The product was pure and did not require recrystallization. The yield of the product was about 100%, and the melting point was 70°–73° C.

Elemental Analysis: Calcd: C 68.18%; H 10.97%. Found: C 68.03%; H 10.92%.

SYNTHESIS EXAMPLE 3

Synthesis of Compound (27), 6-t-butyldimethylsilyloxy-4,4,7,4′,4′,7′-hexamethyl-2,2′-bisspirochroman 11.0 g (0.03 mol) of 6-hydroxy-4,4,7,4′,4′,7′-hexamethyl-2,2′-bisspirochroman was dissolved in 100 ml of dimethylformamide, and then 5.0 g (0.074 mol) of imidazole was added thereto. To the mixture was added a solution of 10.0 g (0.066 mol) of t-butyldimethylsilyl chloride in 10 ml of dimethylformamide. After stirring the mixture for 4 hours at room temperature, 200 ml of ethyl acetate was added thereto and the resultant mixture was washed with water (repeated twice). The organic layer formed was recovered, dried by anhydrous sodium sulfate, and the solvent was distilled off under reduced pressure to provide a crystalline residue, which was recrystallized from acetonitrile to provide 16 g of white crystals. The yield was 89% and the melting point was 153°–155° C.

Elemental Analysis: Calcd.: C 70.41%; H 9.46%. Found: C 70.52%; H 9.49%.

Couplers used in photographic materials according to this invention are as follows:

Yellow couplers are generally closed chain ketomethylene series compounds as described, for example, in U.S. Pat. Nos. 3,341,331, 2,875,057 and 3,551,155, German patent application (OLS) No. 1,547,868, U.S. Pat. Nos. 3,265,506, 3,582,322 and 3,725,072, German patent application (OLS) No. 2,162,899, U.S. Pat. Nos. 3,369,895 and 3,408,194, and German patent application (OLS) Nos. 2,057,941, 2,213,461, 2,219,917, 2,261,361 and 2,263,875.

As magenta couplers, 5-pyrazolone series compounds are generally used, but indazolone series compounds and cyanoacetyl series compounds may also be used. Examples of these magenta couplers are described in U.S. Pat. Nos. 2,439,098, 2,600,788, 3,062,653, and 3,558,319, British Pat. No. 956,261, U.S. Pat. Nos. 3,582,322, 3,615,506, 3,519,429, 3,311,476, 3,419,391 and 3,935,015, German patent application (OLS) No. 2,424,467, German Pat. No. 1,810,464, Japanese Pat. Publication No. 2016/69, German patent application (OLS) No. 2,418,959, Japanese patent application (OPI) No. B 42726/77 (the term "OPI" as used herein refers to a "published unexamined Japanese patent application"), U.S. Pat. No. 2,983,608, German Pat. Nos. 2,532,225 and 2,536,191, and Japanese patent application (OPI) No. 16924/76.

As cyan couplers, phenol derivatives and naphthol derivatives are generally used and examples of such cyan couplers are described in U.S. Pat. Nos. 2,369,929, 2,474,293, 2,698,794, 2,895,826, 3,311,476, 3,458,315, 3,560,212, 3,582,322, 3,591,383, 3,386,301, 2,434,272, 2,706,684, 3,034,892, and 3,583,971, German patent application (OLS) No. 2,163,811, Japanese Pat. Publication No. 28836/70 and Japanese patent application (OPI) No. 122335/74.

Development inhibitor releasing type couplers (so-called DIR couplers), which release development inhibitors in the coupling reaction or other compounds releasing compounds having development inhibiting action at coupling reaction can be used in this invention. Examples of these compounds are described in U.S. Pat. Nos. 3,148,062, 3,227,554, 3,253,924, 3,617,291, 3,622,328 and 3,705,201, British Pat. No. 1,201,110, and U.S. Pat. Nos. 3,297,445, 3,379,529, and 3,639,417.

Colored couplers are also used in this invention and examples of them are described in U.S. Pat. Nos. 2,434,272, 3,476,564, 3,476,560, Japanese patent application (OPI) No. 131448/74, and U.S. Pat. Nos. 3,034,892, 3,386,301, 2,434,272, 3,148,062, 3,227,554, 3,701,783 and 3,617,291.

The amount of the color image stabilizer compounds of the formula (I) or (II) used in this invention depends upon the kind of couplers used, but is generally from about 0.5% to 200% by weight, and preferably from 2% to 150% by weight, based on the weight of the coupler.

In case of using the color image stabilizer compounds of the formula (I) or (II) according to this invention in color diffusion transfer photographic systems (particularly in an image-receiving layer in a diffusion transfer photographic element), the amount of the color image stabilizer compounds of the formula (I) or (II) according to this invention is generally used from about 0.01 to 500 mol/DTR dye and also from about $10^{-5}$ to $5 \times 10^{-1}$ mol/m$^2$, and preferably from 0.1 to 50 mol/DTR dye and also from $10^{-4}$ to $5 \times 10^{-2}$ mol/m$^2$.

If the amount of the color image stabdlizer is below the above-described range, the discoloring and fading prevention effect on the color images, and the discoloring prevention effect on the white ground are very weak, and the use of such a small amount is unsuitable for practical purposes. Also, if the amount is too large, the process of development can be obstructed, and there is a possibility of causing a reduction in color density.

In the practice of this invention, known fading prevention agents may be used together with the color image stabilizers used according to this invention as a mixture thereof, if desired, or the stabilizers according to this invention can be used exclusively.

Examples of known fading preventing agents include the hydroquinone derivatives described in U.S. Pat. Nos. 2,360,290, 2,418,613, 2,675,314, 2,701,197, 2,704,713, 2,738,659, 2,732,300, 2,735,765, 2,710,801 and 2,816,028, and British Pat. No. 1,363,921; gallic acid derivatives described in U.S. Pat. Nos. 3,457,079 and 3,069,262 and Japanese Pat. Publication No. 13496/68; the p-alkoxyphenols described in U.S. Pat. Nos. 2,735,765 and 3,698,909 and Japanese Pat. Publication No. 20977/74; and the p-oxyphenol derivatives described in U.S. Pat Nos. 3,432,300, 3,573,050, 3,574,627 and 3,764,337.

The color image stabilizer of this invention can be incorporated in photographic layers of silver halide color photographic materials in the following manners. For example, the stabilizer compound can be dissolved in a low boiling organic solvent such as ethyl acetate, ethanol, etc., and the solvent is directly (without being emulsified) added to a silver halide emulsion or a mixed solution of coupler dispersions. However, it is desirable that the color image stabilizer of this invention be dissolved in a high boiling solvent such as dibutyl phthalate, tricresyl phosphate, etc., together with a coupler and, if necessary, a low boiling auxiliary solvent, the solution is dispersed as oil droplets in an aqueous solution of water-soluble protective colloid such as gelatin, and the emulsified dispersion thus obtained is added to a silver halide emulsion or an emulsified dispersion of the color image dispersion of this invention is prepared and the dispersion is added to a silver halide emulsion together with a coupler dispersion.

The color image stabilizers of this invention are incorporated in photographic layers such as coupler-containing silver halide photographic emulsion layers (e.g., red-sensitive silver halide emulsion layers, green-sensitive silver halide emulsion layers, and blue-sensitive silver halide emulsion layers) as well as nonphotosensitive photographic auxiliary layers (e.g., protective layers, filter layers, interlayers, subbing layers, etc.), but it is particularly preferred to incorporate the color image stabilizer of this invention in a magenta coupler-containing silver halide photographic layers and in this case, the incorporation of the compound is particularly effective for the prevention of discoloring and fading of magenta color images.

Typical examples of the high boiling organic solvent used for dispersing the color image stabilizer of this invention solely or together with a coupler are butyl phthalate, dinoyl phthalate, butyl benzoate, diethylhexyl sebacate, butyl stearate, dinonyl maleate, tributyl citrate, tricresyl phosphate, dioctylbutyl phosphate, trihexyl phosphate, trioctadecyl phosphate, etc., solvents as described in U.S. Pat. No. 3,676,137, as well as diethyl citrate, dioctyl adipate, 3-ethylbiphenyl, and the liquid dye stabilizers described in *Product Licensing Index*, Vol. 83, pp. 26–29 (March, 1971) under the title of "Improved Type Photographic Dye Image Stabilizers".

Examples of the low boiling organic solvent which can be used as an auxiliary solvent together with the high boiling organic solvent include ethyl acetate, butyl acetate, ethyl propionate, ethyl formate, butyl formate, nitroethane, carbon tetrachloride, chloroform, hexane, cyclohexane, ethylene glycol, acetone, ethanol, dimethylformamide, dioxane, etc., and benzene, toluene, oxylene, etc., may be added to these solvents.

In the case of dispersing a solution of the color image stabilizer of this invention either solely or together with a coupler in an aqueous solution of a water-soluble colloid, a surface active agent is used. Examples thereof include sodium alkylsulfosuccinate, sodium alkylbenzenesulfonate, etc., and examples of the hydropholic protective colloid are gelatin, casein, carboxymethyl cellulose, polyvinyl alcohol, polyvinyl pyrrolidone, styrene-maleic anhydride copolymer, a condensation product of a styrene-maleic anhydride copolymer and polyvinyl alcohol, a polyacrylate, ethyl cellulose, etc., although the invention is not limited to these materials.

Supports usually used for photographic materials are used as the supports of the color photographic materials of this invention. Examples thereof include cellulose nitrate films, cellulose acetate films, cellulose acetate butyrate films, cellulose acetate propionate films, polystyrene films, polyethylene terephthalate films, polycarbonate films, laminates of these films, thin glass sheets, papers, etc. Barytacoated papers, papers coated or laminated with an α-olefin polymer, particularly a polymer of an α-olefin having from 2 to 10 carbon atoms, such as polyethylene, polypropylene, ethylene-butene copolymer, etc., and plastic films, the surfaces of which have been roughened to improve the adhesion with other polymers as described in Japanese Pat. Publication No. 19068/72, can be also used with good results.

These supports may be transparent or opaque according to the purpose of color photographic materials. Also, transparent support colored by the addition of a dye or pigment may be used in this invention.

Opaque supports include papers which are originally opaque, opaque films prepared by adding a dye or a pigment (such as titanium oxide) to transparent films, plastic films surface-treated by the method described in Japanese Pat. Publication No. 19068/72, and papers or plastics which are rendered completely light blocking by the addition of carbon black, dyes, etc.

A subbing layer is ordinarily formed on the support. For further improving the adhesion of the support with polymers or photographic emulsions, the surface of the support may be subjected to a pretreatment such as corona discharging, ultraviolet irradiation, frame treatment, etc.

Discoloring or fading of the silver halide color photographic material of this invention can be even more effectively prevented by forming an ultraviolet absorbing layer on the surface of the photographic silver halide emulsion layers which are image-forming layers.

For processing the silver halide color photographic materials of this invention, any color processing agents such as color developing agents, bleaching agents, fixing agents, etc., can be used without particular restrictions. In particular, the invention can be advantageously applied to the technique on the low-silver type color photographic materials described in U.S. Pat. No. 3,902,905. Furthermore, an intensifying agents for the color intensification described in Japanese patent application (OPI) No. 9728/73, and Japanese patent application (OPI) No. 53826/76.

The invention can be applied to ordinary color photographic materials particularly to color photographic materials for printing and further can be applied to the color photographic systems, in particular color diffusion transfer photographic systems (i.e., an image-receiving layer in a diffusion transfer photographic element) described in U.S. Pat. Nos. 3,227,550, 3,227,551, 3,227,552 and U.S. Pat. No. B351,673.

For obtaining dye images using the color photographic materials of this invention, color development processing must be conducted after imagewise exposure. The color photographic development process includes essentially a color development, a bleach, and fix. Two steps may be made in one step. A system composed of a color development, a first fix, and a blix can be employed. The development process can also include, if necessary, a pre-hardening bath, a neutralization bath, a first development (black-and-white development), an image stabilization bath, wash, etc. The processing temperature is usually above 18° C., and preferably from 20° to 60° C.: recently, the range of 30° to 60° C. has become preferred.

The color developer used for the color development is an aqueous alkali solution containing an aromatic primary amino color developing agent and having a pH above 8, preferably from 9 to 12. Preferred examples of the color developing agent are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy,-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline and the salts (e.g., sulfates, hydrochlorides, sulfites, p-toluenesulfonates, etc.) of these compounds. Other examples are described in U.S. Pat. Nos. 2,193,015 and 2,592,364, Japanese patent application (OPI) No. 64933/73 and L. F. A. Mason, *Photographic Processing Chemistry*, pp. 226–229 (1966) by Focal Press-London.

The color developer can further contain a pH buffer such as the sulfite, carbonate, borate, and phosphate of an alkali metal as well as a development inhibitor or an anti-foggant such as a bromide, an iodide and an organic anti-foggant.

Practical examples of the anti-foggants are potassium bromide; potassium iodide; the nitrobenzimidazoles described in U.S. Pat. Nos. 2,656,271 and 2,496,940; mercaptobenzimidazole; 5-methylbenzotriazole; 1-phenyl-5-mercaptotetrazole; the compounds described in U.S. Pat. Nos. 3,113,864, 3,342,596, 3,295,976, 3,615,522 and 3,597,199; the thiosulfonyl compounds described in British Pat. No. 972,211; the phenazine-N-oxides described in Japanese Pat. Publication No. 41675/71; and the anti-foggants described in *Kagaku Shashin Binran* (*Handbook for Scientific Photography*), Vol. 2, p. 47.

Also, the color developer may, if necessary, further contain a water softener; preservatives such as hydroxylamine, etc.; organic solvents such as benzyl alcohol, diethylene glycol, etc.; development accelerator such as polyethylene glycol, a quaternary ammonium salt, an amine, etc.; dye-forming couplers, competing couplers; fogging agents such as sodium borohydride, etc.; auxiliary developing agents such as 1-phenyl-3-pyrazolidone; and tackifiers.

The color photographic materials of this invention are processed by ordinary color development process but may be processed by the following color intensification developing process. Examples of such processes using peroxides are described in U.S. Pat. Nos. 3,674,490 and 3,761,265, German patent application (OLS) No. 2,056,360, Japanese patent application (OPI) Nos. 6338/72, 10538/72, 13335/77, 13334/77 and 13336/77; processes using cobalt complex salts are described in German patent application (OLS) No. 2,226,770, Japanese patent application (OPI) Nos. 9728/73, 9729/73, 6026/76, 94822/76, 133023/76, 7728/77 and 11034/77; and further a process using chlorous acid is described in Japanese patent application (OPI) Nos. 53826/76, 99022/76 and 103430/76.

Silver halide photographic emulsion layers after color development are ordinarily bleached. The bleach processing may be practiced together with a fix processing at the same time or separately from fix processing. As bleaching agents, there are compounds of polyvalent metals such as iron (III), cobalt (III), chromium (VI), copper (II), etc., peroxides, quinones, nitroso compounds. Preferred examples include ferricyanides, dichromates, organic complex salts of iron (III) or cobalt (III), polyaminopolycarbonates such as ethylenediaminetetraacetic acid, nitrilotriacetic acid, 1,3-diamino-2-propanoltetraacetic acid, etc., complex salts of an organic acid such as citric acid, tartaric acid, maleic acid, etc., persulfates, permanganates, nitrosophenol, and the like. In these materials, potassium ferricyanide, ethylenediaminetetraacetic acid iron (III) sodium and ethylenediaminetetaacetic acid iron (III) ammonium are particularly useful. An ethylenediaminetetraacetic acid iron (III) complex salt is useful in a bleach solution and in a mono-bath blix solution.

The bleach solution or a blix solution may further contain bleach accelerators as described in U.S. Pat. Nos. 3,042,520 and 3,241,966 and Japanese Pat. Publication Nos. 8506/70 and 8836/70 and other various additives.

Then, the invention will be practically described by the following examples.

EXAMPLE 1

10 g of a magenta coupler, 1-(2,4,6-trichlorophenyl)-3-[(2-chloro-5-tetradecanamido)anilino]-2-pyrazolin-5-one (Compound A) was dissolved in 20 ml of tricresyl phosphate and 20 ml of ethyl acetate, and the solution was dispersed by emulsification in 80 g of an aqueous 10% gelatin solution containing 8 ml of an aqueous solution of 1% sodium dodecylbenzenesulfonate.

Then, the emulsified dispersion was mixed with 145 g (containing 7 g as Ag) of a green-sensitive silver chlorobromide emulsion (50% Br) and after adding sodium dodecylbenzenesulfonte thereto, the mixture was coated on a paper support laminated with polyethylene at both surfaces, to provide Sample A. The coupler coverage of Sample A was 400 mg/m$^2$.

In the same manner as above, except that 3 g of each of the compounds of this invention shown in Table I and the comparison compounds shown below was added instead of Compound A in preparing emulsified dispersions, Samples B through I were prepared.

Each of the samples was exposed through continuous wedge for 1 second at 1,000 lux and processed by the following processing steps.

| Processing Step | Temperature | Time |
| --- | --- | --- |
| Development | 33° C. | 3 min 30 sec |
| Blix | 33° C. | 1 min 30 sec |
| Wash | 28–35° C. | 3 min |

The compositions of the processing solutions used in the above processing were as follows:

| Developer | |
| --- | --- |
| Benzyl alcohol | 15 ml |
| Diethylenetriaminepentaacetic acid | 5 g |
| Potassium bromide | 0.4 g |
| Na$_2$SO$_3$ | 5 g |
| Na$_2$CO$_3$ | 30 g |
| Hydroxylamine sulfate | 2 g |
| 4-Amino-3-methyl-N-ethyl-N-$\beta$-(methanesulfonamido)ethylaniline . 3/2H$_2$SO$_4$ . H$_2$O | 4.5 g |
| Water to make | 1,000 ml |
| | pH 10.1 |

| Blix Solution | |
| --- | --- |
| Ammonium thiosulfate (70 wt%) | 150 ml |
| Na$_2$SO$_3$ | 5 g |
| Na[Fe(EDTA)] | 40 g |
| EDTA | 4 g |
| Water to make | 1,000 ml |
| | pH 6.8 |

Each sample having dye images thus formed was then subjected to a fading test for 5 days by a xenon tester (illuminance of 200,000 lux) using a Fuji Film ultraviolet absorbing filter cutting-out light of wavelengths below 400 nm. The density change of the portion having an initial density of 2.0 and the density change of the white ground portion were measured by means of a Macbeth densitometer RD-514 (Status AA Filter). The results are shown in Table I.

TABLE I

| Sample | Color Image Stabilizer | Yellow Density Change* | Magenta Density Change** | Note |
| --- | --- | --- | --- | --- |
| A | — | +0.28 | −1.32 | Comparison |
| B | Compound (3) | +0.06 | −0.23 | Invention |
| C | Compound (16) | +0.04 | −0.20 | Invention |
| D | Comparison Compound (a) | +0.06 | −0.63 | Comparison |
| E | Comparison Compound (b) | +0.19 | −0.59 | Comparison |
| F | Comparison Compound (c) | +0.14 | −0.41 | Comparison |
| G | Compound (26) | +0.07 | −0.21 | Invention |
| H | Comparison Compound (d) | +0.20 | −0.65 | Comparison |
| I | Comparison | +0.20 | −0.67 | Comparison |

TABLE I-continued

| Sample | Color Image Stabilizer | Yellow Density Change* | Magenta Density Change** | Note |
|---|---|---|---|---|
| | Compound (e) | | | |

*Density change in white ground portion.
**Initial density was 2.0.

The comparison compounds used in this experiment were as follows:

Comparison Compound (a)

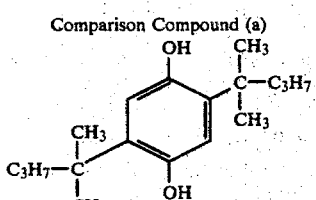

Comparison Compound (b)

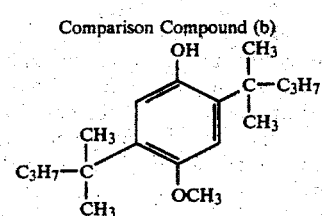

Comparison Compound (c)

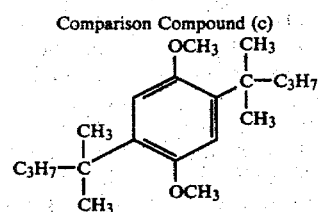

Comparison Compound (d)

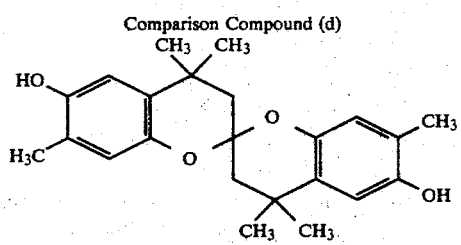

Comparison Compound (e)

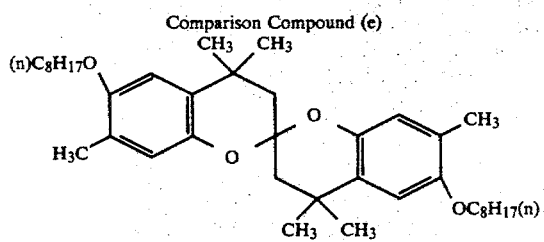

From the results, it is clear that the compounds of this invention are effective for the light fading prevention of color images, and also for the prevention of yellowing of white ground portions, by light.

EXAMPLE 2

In the same manner as for preparing Sample A in Example 1, and using the same magenta coupler compound as used in Example 1, a coating composition for the third layer as shown in Table III was prepared and a multilayer photographic sample of Table III containing the third layer was prepared (Sample J). Also, multilayer samples (Sample K and Sample L) were prepared in the same manner as the case of preparing Sample J, using coating compositions for the third layer having the same composition as above except that 3 g or 6 g of Compound (16) of this invention was added to 10 g of the coupler as in the above case. Also, by following the above manner, Comparison Samples M and O and the Sample N of this invention were prepared. Each of the samples was exposed and processed as in Example 1 and the samples having dye images thus formed were subjected to a fading test for 4 weeks by means of a fluorescent lamp Fade-o-meter (made by Shimazu Scientific Instrument & Equipment) (20,000 lux). The results are shown in Table II.

TABLE II

| Sample | Color Image Stabilizer | Amount* (g) | Magenta Density Change** | Note |
|---|---|---|---|---|
| J | — | — | −0.82 | Comparison |
| K | Compound (16) | 3 | −0.16 | Invention |
| L | Compound (16) | 6 | −0.09 | Invention |
| M | Comparison Compound (a) | 3 | −0.32 | Comparison |
| N | Compound (16) Comparison Compound (a) | 3 3 | −0.12 | Invention |
| O | Comparison Compound (c) | 3 | −0.35 | Comparison |

*The amount per 10 g of coupler.
**Initial density was 1.0.

From the results, it is clear that the compound of this invention is effective for the light fading preventing of color images, and the effect increased with additional amounts thereof and with the use of a known fading preventing agent such as Comparison Compound (a).

The layer structure of Sample J is shown in Table III.

TABLE III

| | |
|---|---|
| The 6th layer: | Protective layer containing gelatin at a coverage of 1,000 mg/m² |
| The 5th layer: | Red-sensitive layer containing silver chlorobromide (50 mol% Br and silver coverage of 300 mg/m²), gelatin at a coverage of 1,000 mg/m², a cyan coupler *1 at a coverage of 400 mg/m² and a coupler solvent *2 at a coverage of 200 mg/m² |
| The 4th layer: | Interlayer containing gelatin at a coverage of 1,200 mg/m², an ultraviolet absorbent *3 at a coverage of 1,000 mg/m², and an ultraviolet absorbent solvent *2 at a coverage of 250 mg/m² |
| The 3rd layer: | Green-sensitive emulsion layer containing silver chlorobromide emulsion (50 mol % Br and silver coverage of 290 mg/m²), gelatin at a coverage of 1,000 mg/m², a magenta coupler *4 at a coverage of 200 mg/m², and a coupler solvent *5 at a coverage of 200 mg/m² |
| The 2nd layer: | Interlayer containing gelatin at a coverage of 1,000 mg/m² |
| The 1st layer: | Blue-sensitive emulsion layer containing silver chlorobromide emulsion (80 mol % Br and a silver coverage of 400 mg/m²), gelatin at a coverage of 1,200 mg/m², a yellow coupler *6 at a coverage of |

TABLE III-continued

|  |  |
|---|---|
|  | 300 mg/m², and a coupler solvent *7 at a coverage of 150 mg/m² |
| Support: | Paper support laminated with polyethylene at the both surfaces |
| (*1) Coupler: | 2-[α-(2,4-di-tert-pentylphenoxy)-butanamido]-4,6-dichloro-5-methylphenol |
| (*2) Solvent: | dibutyl phthalate |
| (*3) Ultraviolet absorbent: | 2-(2-hydroxy-3-sec-butyl-5-tert-butylphenyl)benzotriazole |
| (*4) Coupler: | 1-(2,4,6-trichlorophenyl)-3-[(2-chloro-5-tetradecanamido)anilino]-2-pyrazolin-5-one |
| (*5) Solvent: | tricresyl phosphate |
| (*6) Coupler: | α-pivaloyl-α-(2,4-dioxo-5,5'-dimethyl-oxazolidin-3-yl)-2-chloro-5-[α-(2,4-di-tert-pentylphenoxy)butanamido]acetanilide |
| (*7) Solvent: | dioctylbutyl phosphate |

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a photographic layer containing at least one of the compounds represented by the formula (I) or (II)

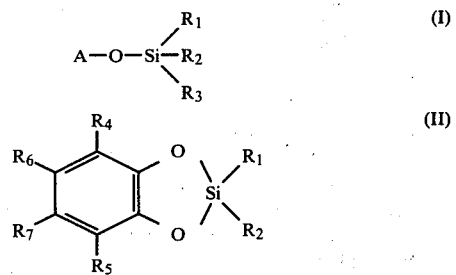

wherein A represents an aryl group; $R_1$, $R_2$ and $R_3$ each represents hydrogen, a halogen atom, an alkyl group, or an aryl group except that $R_1$, $R_2$, and $R_3$ cannot all be hydrogen; $R_4$ and $R_5$ each represents hydrogen, a halogen atom, an alkyl group, an aryl group, an alkoxy group, an alkylthio group, an acyl group, an aryloxy group, a carboxy group, a sulfo group, or a hydroxy group; and $R_6$ and $R_7$ each represents hydrogen, a halogen atom, an alkyl group, an aryl group, an alkoxy group, an aryloxy group, an alkylthio group, an acyl group, or a hydroxy group; or $R_6$ and $R_7$ together form an

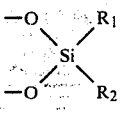

group or a 5-membered or 6-membered carbocyclic or heterocyclic ring.

2. A silver halide color photographic material as in claim 1 comprising a photographic layer containing a compound represented by the formula (I).

3. A silver halide color photographic material as in claim 1 comprising a photographic layer containing a compound represented by the formula (II).

4. A silver halide color photographic material as in claim 1, 2, or 3 wherein the photographic layer containing the compound is a magenta coupler-containing green-sensitive silver halide emulsion layer.

5. A silver halide color photographic material as in claim 1, 2, or 3 wherein the photographic layer containing the compound is a cyan coupler-containing red-sensitive silver halide emulsion layer.

6. A silver halide color photographic material as in claim 4 wherein the amount of compounds represented by the formulae (I) and (II) is from 0.5% to 200% by weight based on the weight of the coupler.

7. A silver halide color photographic material as in claim 5 wherein the amount of compounds represented by the formulae (I) and (II) is from 0.5% to 200% by weight based on the weight of the coupler.

8. A silver halide color photographic material as in claim 4 wherein the amount of compounds represented by the formulae (I) and (II) is from 2% to 150% by weight based on the weight of the coupler.

9. A silver halide color photographic material as in claim 5 wherein the amount of compounds represented by the formulae (I) and (II) is from 2% to 150% by weight based on the weight of the coupler.

10. A silver halide color photographic material as in claim 1 or 2 wherein A represents a substituted or unsubstituted phenyl or naphthyl group or a chroman, spirochroman, indan or spiroindan ring having an

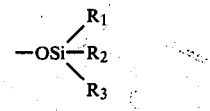

on the phenyl moiety thereof.

11. A silver halide color photographic material as in claim 10 wherein A represents a substituted phenyl group containing a halogen atom, an alkyl group, an alkoxy group, an alkoxycarbonyl group, an acyloxy group, an alkoxycarbonyloxy group, an alkylthio group or a hydroxy group as the substituent.

* * * * *